United States Patent [19]

Pappas et al.

[11] Patent Number: 5,047,062
[45] Date of Patent: Sep. 10, 1991

[54] FEMORAL STEM-TYPE PROSTHESIS

[76] Inventors: Michael J. Pappas, 61 Gould Pl., Caldwell, N.J. 07006; Frederick F. Buechel, 76 Crest Dr., South Orange, N.J. 07079

[21] Appl. No.: 458,595

[22] Filed: Dec. 29, 1989

Related U.S. Application Data

[60] Continuation of Ser. No. 825,985, Feb. 4, 1986, abandoned, which is a division of Ser. No. 574,037, Jan. 26, 1984, abandoned.

[51] Int. Cl.⁵ .............................................. A61F 2/32
[52] U.S. Cl. .................................................... 623/23
[58] Field of Search ...................... 623/16, 18, 19, 20, 623/22, 23

[56] References Cited

U.S. PATENT DOCUMENTS 4,001,897  1/1977  Rambert ................................ 623/23
4,080,666  3/1978  Fixel ..................................... 623/23

FOREIGN PATENT DOCUMENTS 2247721  4/1974  Fed. Rep. of Germany ........ 623/23
2645100  4/1978  Fed. Rep. of Germany ........ 623/23
1527498  10/1978  United Kingdom .................. 623/23

*Primary Examiner*—David J. Isabella
*Attorney, Agent, or Firm*—Anthony J. Casella; Gerald E. Hespos

[57] ABSTRACT

An improved stem-type prosthesis, including a head, stem and neck providing reduced bending and shear loading of the neck thereby allowing the use of a smaller neck to improve the range of motion between the prosthesis and an acetabular cavity and to allow the use of a more complete spherical head thereby improving wear and separation resistance of the prosthesis from other components such as from an acetabular component.

8 Claims, 9 Drawing Sheets

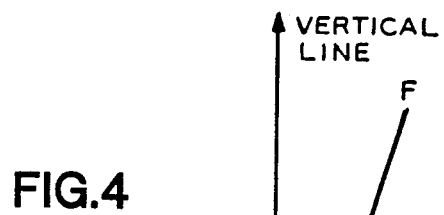
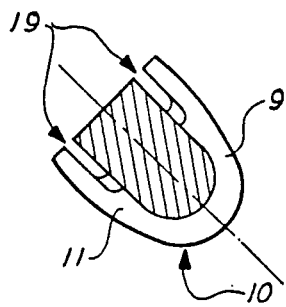
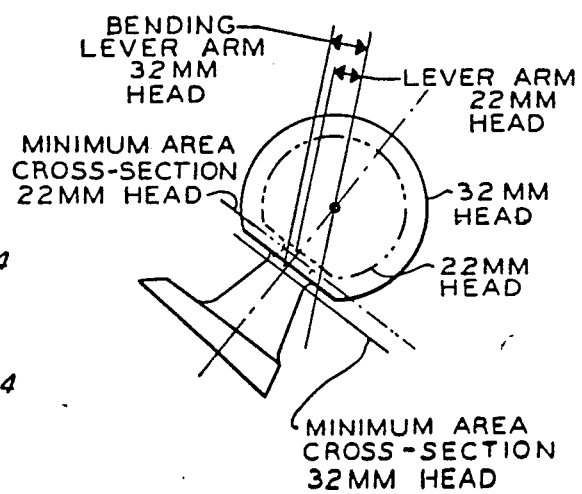

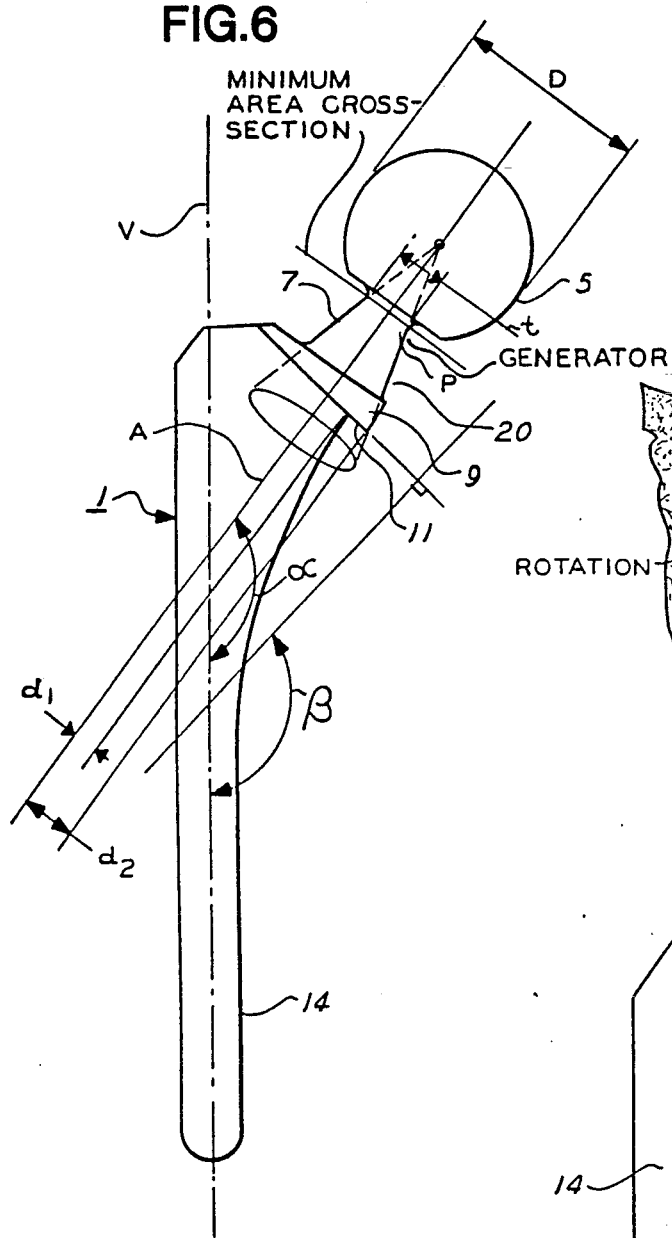
FIG.6
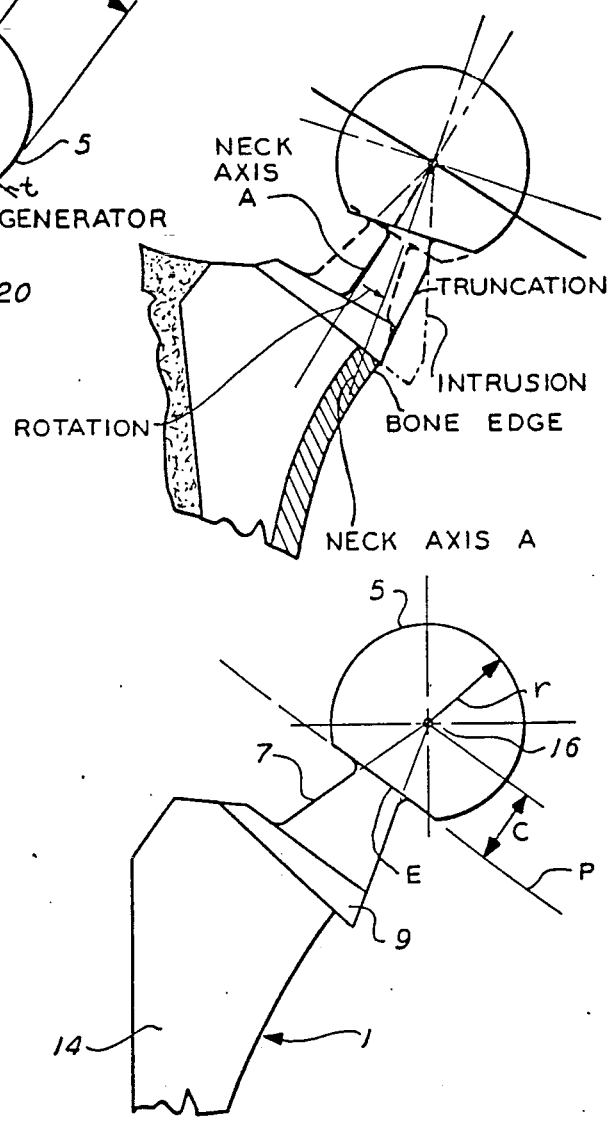
FIG.8
FIG.9

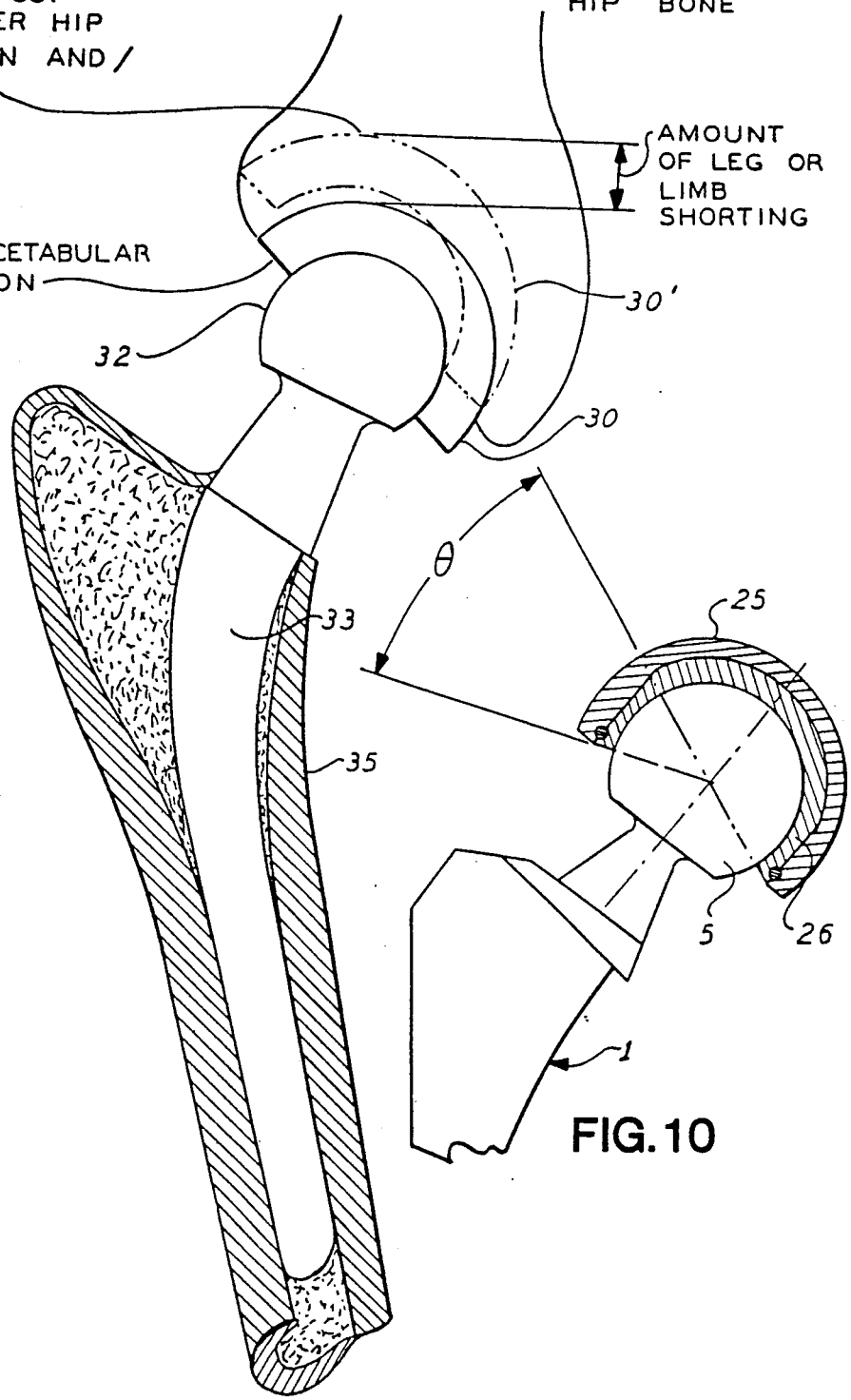

FEMORAL STEM-TYPE PROSTHESIS

This application is a continuation of prior application Ser. No. 825,985 filed on Feb. 4, 1986, now abandoned, which is a divisional of application Ser. No. 574,037 filed on Jan. 26, 1984, now abandoned.

BACKGROUND OF THE INVENTION

This invention relates generally to an improved stem-type prosthesis and more particularly relates to a stem-type femoral prosthesis particularly useful in artificial hip joints and of the type including a head, neck and stem, and in some embodiments a collar and still more particularly relates to an improved extended neck stem-type prosthesis.

Stem-type femoral prostheses generally include a spherical head, neck and stem and are generally fixtured into the medullary cavity of the proximal end of the femur by the use of cement as described in U.S. Pat. No. 4,021,865 issued May 10, 1977 to John Charnley or by use of biological fixation into porous surfaces as described in U.S. Pat. No. 4,156,943 issued June 5, 1979 to John P. Collier and in U.S. Pat. No. 3,808,606 issued May 7, 1974 to Raymond G. Tronzo or by direct insertion into the proximal femur without the use of cement or a porous or roughened surface as described in U.S. Pat. No. 4,031,571 issued June 28, 1977 to Gunther Heimke et al.

In U.S. Pat. No. 4,141,088 issued Feb. 27, 1979 to James T. Treace there is described a hip prosthesis wherein the femoral stem prosthesis uses a neck portion whose cross-sectional area is narrower in its anterior-posterior dimension than in its medial-lateral dimension (note FIGS. 1 and 2). The use of non-circular neck cross-section for the purpose of improving the range of motion of the artificial joint is an important attribute because of significant problems of the dislocation of a joint resulting from inadequate motion range. The Treace patent also describes a technique wherein prostheses with varying neck length are made so that the distance from the center of the head to a line passing along the lateral border of the stem or the stem axis is held constant so that a specified anatomical distance is always maintained.

The head of the femoral prosthesis, as noted above, is generally spherically shaped and articulates either with the natural acetabulum or with an acetabular replacement such as disclosed in U.S. Pat. No. 3,722,002 issued May 27, 1973 to John Charnley, U.S. Pat. No. 3,829,904 issued Aug. 20, 1974 to Robin Ling et al., and U.S. Pat. No. 3,848,272 issued Nov. 19, 1974 to Douglas G. Noiles or U.S. Pat. No. 3,863,273 issued Feb. 4, 1975 to Robert G. Averill and U.S. Pat. No. 3,982,281 issued Sept. 28, 1976 to Richard P. Giliberty. This articulation occurs during walking and other normal human activities during which loads are transmitted across the hip joint. Thus, load must be transferred from the proximal femur to the pelvis. In particular, loads transmitted by the acetabulum or acetabular component to the spherical head of the femoral prosthesis must be transmitted by the neck to the stem. In addition, many prostheses employ a calcar collar so that load may be transmitted through the neck and collar directly to the calcar in addition to the transmittal of load by, the stem through the intramedullary canal to the femoral shaft. Collars are generally of two types: those such as shown in the Heimke et al. patent where the collar is distinct from the neck and those as shown in the Charnley and Treace patents where the collar is simply the inferior surface of the neck region. Typical of the collarless design is the stem disclosed in U.S. Pat. No. 4,310,931 issued Jan. 19, 1982 to Muller.

In general, the direction of the resultant joint reaction load on the head of the femoral component is not coincident with the locus of the centroids of the cross-sections of the neck. As the result, joint loading generally introduces bending and shear loading on the neck in addition to the compressive load which would result were the force vector coincident with the centroid locus; as a result, bending, shear and compressive stresses exist in the neck. As used herein, a neck axis is defined as a line connecting the centroid of the cross-section of the most proximal region of the neck with a centroid of a cross-section of the most distal region of the neck where such centroids include only the neck regions and are taken perpendicular to the neck axis. Generally, the axis of the neck is oriented relative to the joint reaction load so that for most of the loading conditions encountered during walking and other activities, significant bending loads are applied to the neck such that the lateral surface of the neck encounters tensile stresses. Such tensile stresses are particularly harmful since fatigue fracture is primarily a tensile phenomenon wherein a local imperfection produces a stress magnification effect which results in the initiation of a crack. The crack tip itself then is a stress riser producing the stress magnification and the continuing removal and application of load as experienced during human activity can produce slow propagation of this crack until catastrophic failure of the neck occurs. Shearing loads can also produce tensile stresses, and the noted fatigue fracture can result from the application of shearing loads. Compressive loading, however, cannot produce tensile stresses. As a result, where fatigue loading is present it is desirable to eliminate or minimize tensile stresses by minimizing or eliminating bending and shear loading. Unfortunately, it is impossible to completely eliminate bending and shear since the orientation of the resultant load vector on the hip changes relative to any predetermined neck axis orientation during normal activity and thus it is impossible to completely eliminate bending and shear effects.

The hip joint reaction load varies in magnitude and orientation relative to a given reference frame fixed to the pelvis. Further, the joint reaction load varies in direction relative to a reference frame fixed in the femur. However, the major variation in the direction of the joint reaction load relative to the femur occurs in the femoral plane which is defined herein as the plane defined by the center of the natural or replacement femoral head, the distal tip of the femoral stem or the corresponding point on the proximal femur into which the femoral stem is implanted and the centroid of a cross-section of the most proximal portion of the femoral stem where such cross-section is taken perpendicular to the neck axis or a corresponding point on the femur were such prosthesis implanted therein.

Typical variation of the load in the femoral plane is illustrated in FIG. 1 where in this figure line A lies in a vertical plane during two legged stance. The angle $\gamma$ is defined as the angle measured from line A to the force vector component in the femoral plane and varies from 0° during two-legged stance where the joint reaction load is less than one half times body weight to about 20° during human activities which produce relatively high joint reaction loads which are on the order of several times body weight.

The stress condition resulting from a combination of bending and compression is shown in FIG. 2. The two loading conditions produce a combined stress state which can be determined by simply adding the stresses resulting from pure bending and pure compression loading individually. It may be seen that the bending stress increases the maximum value of the compressive stress resulting from the combined loading and also where bending is sufficient can produce tensile stresses as a result of the comb loading. Where shear is present, since magnitude of the stress is a function not only of loading but of orientation, one can always find an orientation where shear stresses are absent and this stress state consists only of tension and compression. These tension and compressive stresses are commonly called the principal stresses. Thus, one has an analogous case where one has tension, shear and compression loading.

Typically, the heads of femoral prostheses are truncated spheres as shown in the U.S. Patents noted above to Charnley, Treace and Muller terminating in a truncation plane which plane is defined herein as the plane including at least three points on the truncation edge of the spherical surface. Although the patent literature, for example U.S. Pat. No. 3,843,975 issued Oct. 29, 1974 to Raymond G. Tronzo and the above-noted Heimke et al. patent, shows drawings of spherical heads which do not terminate in a truncation edge, these drawings are merely patent draftsman or artistical representations of femoral stems and the head configurations shown do not represent actual embodiments of a true prosthetic femoral head. These patents generally relate to the stem of the femoral prosthesis and the head is depicted for the purpose of providing a complete drawing and obviously is not intended to represent an actual prosthetic femoral head. More particularly, the femoral head shown in the Tronzo patent is inaccurate since the intersection between what is apparently a round neck and a spherical head cannot possibly result in the curved line shown. Most actual femoral head embodiments result in a partial spherical head wherein the spherical segment is only slightly greater than a hemisphere as typified by those disclosed in the Charnley and Muller patents and which represent actual head neck embodiments; the drawings in these latter two patents are, in fact, drawings of commercially available prostheses. Such truncation can produce a situation as shown in FIG. 3 where the truncation edge E enters the acetabular cavity C of an acetabular bearing member A and results in the edge E rubbing over the acetabular bearing surface B. This situation produces a stress riser at the edge in the bearing B accelerating bearing wear. Further, such truncation of femoral heads can reduce the separation strength as described in the Biomedical Engineering Corp. TECHNICAL REPORT, "Technical Considerations in the Selection of a Femoral Endoprosthesis," Pappas, M. J. and Buechel, F. F., published 1982, as compared to the separation strength of femoral heads which are more fully spherical.

It is common practice in the prior art to provide stem-type femoral prostheses of a given size stem with various neck lengths, particularly extended neck lengths, which are intended to compensate on revision for shortening of the leg resulting from hip and/or femur bone erosion; revision being the term used by those skilled in the art to describe generally the replacement of a previously implanted prosthesis by another prosthesis due primarily to the malfunction or loosening of the previously implanted prosthesis. This situation is illustrated in FIG. 11 where due to hip bone erosion and/or removal of additional hip bone in revision, the acetabular cup prosthesis 30 which articulates with the head 32 of the stem-type femoral prosthesis 33 will occupy the position shown in dashed outline instead of the originally implanted position shown in solid outline. Such acetabular cup positioning upon revision causes what is referred to in the art as limb or leg shortening with the amount of shortening also being shown in FIG. 11. Leg or limb shortening is also caused by sinking of the femoral prosthesis 32 downwardly into the femur 35, and upon revision of the femoral prosthesis 33, it would occupy a lower position than is shown in solid outline in FIG. 11.

The most common prior art practice in use to extend neck length to overcome leg shortening is to use a common neck angle $\alpha$ and simply make the neck longer; such an extension is shown in dashed outline and superimposed on an originally implanted femoral prosthesis 37 which is to be revised and which is shown in solid outline in FIG. 12. As will be further noted from FIG. 12, the stem bending moment of the revision prosthesis 36 is increased with such a method of neck extension since the bending lever arm L2 is increased in length as compared to the bending lever arm L1 of the originally implanted prosthesis 37.

As shown in FIG. 14, using the method of neck extension described in the above-noted Treace patent to provide a constant head-stem distance between the lateral edge 41 or the stem axis 43 and the head center 44 of the extended neck prosthesis 45 and the head center 46 of the originally implanted prosthesis 47, the abductor muscle lever arm L4 (distance L2 between the line of action 40 of the abductor muscle and the head center 44 of the extended neck prosthesis 45) is reduced as compared to the anatomical or originally implanted abductor muscle lever arm L3 (distance D1 between the line of action 40 of the abductor muscle and the head center 46 of the originally implanted prosthesis 47) thereby reducing the effectiveness of the abductor muscle and increasing the joint reaction load.

The present invention, inter alia, as taught in detail below, provides a solution to this prior art leg or limb shortening-neck extension problem.

SUMMARY OF THE INVENTION

This invention provides an improved stem-type prosthesis including a head, stem and neck providing reduced bending and shear loading of the neck thereby allowing the use of a smaller neck to improve the range of motion between the prosthesis and an acetabular cavity and to allow the use of a more complete spherical head thereby improving wear and separation resistance of the prosthesis from other components such as from an acetabular component.

DESCRIPTION OF THE DRAWINGS

FIG. 4 shows a stem-type femoral prosthesis emobodying the present invention and implanted in a femur shown in cross-section with the natural femoral head shown in phantom;

FIG. 5 is a cross-sectional view taken along the line 5—5 in FIG. 4 and in the direction of the arrows;

FIG. 6 shows a stem-type femoral prosthesis and illustrates the definitions of the neck dimension t, femoral head diameter D, neck angle $\alpha$, collar angle $\beta$, medial stem distance d1, and medial collar distance d2;

FIG. 7 is an illustration of how the relationship between the head diameter D and neck dimension t increases bending if the neck angle $\alpha$ is such that bending occurs;

FIG. 8 is a partial view of a stem-type femoral prosthesis and illustrates that if the neck axis is rotated counterclockwise excessively to achieve medialization, such will result in truncation of the neck cone or the intrusion of the neck into the space beyond the borders of the bone formerly occupying its normal anatomical position.

FIG. 9 is a partial view of a stem-type femoral prosthesis and illustrates the definitions of the "spherical completeness index," the truncation plane P, the distance c between the truncation plane P and the spherical center of the femoral head and the spherical radius r of the femoral head;

FIG. 10 is a cross-sectional view, taken in the femoral plane, illustrating the overlap angle $\theta$;

FIG. 11 is a generally cross-sectional view, taken in the femoral plane, illustrating the reduction in leg length resulting from bone erosion and/or revision;

DESCRIPTION OF THE PREFERRED EMBODIMENT

Figure 1:
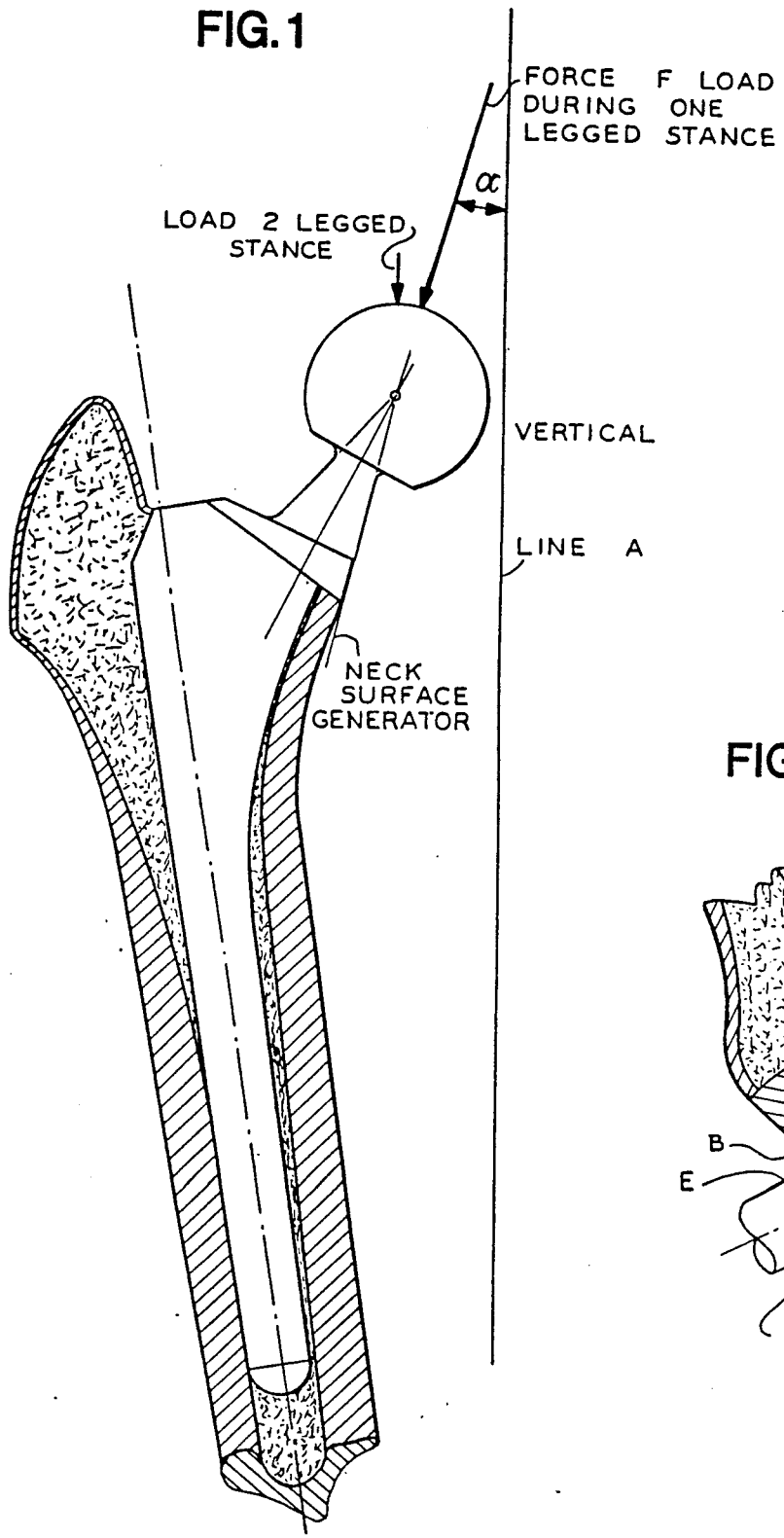
FIG. 1 shows a stem-type femoral prosthesis implanted in a femur (shown in cross-section) and illustrates load variation on the prosthesis in the femoral plane.

FIG. 4 shows a stem-type femoral prosthesis 1 embodying the present invention and implanted in the proximal femur 2; the prosthesis 1 includes a head 5, neck 7, collar 9, and stem 14. The femur consists of an outer shell of cortical bone 3 with an inner cancellous bone 4. The head 5 of the femoral component is highly polished and articulates with a natural acetabulum or an acetabular prosthesis. It should be noted that in the subject prosthesis the center of the spherical prosthetic head 5 coincides closely with the center of the generally spherical natural femoral head 6 shown in phantom.

In the present invention, the neck 7 is positioned as closely as possible to the medial superior edge 8 of the femur 2. Such extreme medial placement of the neck produces for a given head location relative to the shaft the minimal amount of bending stress. Since in this neck configuration the bending stress produces tensile stress on the surface of the neck and since tensile stress is primarily indicated in fatigue fracture which would be the most likely failure mode for the neck, this loading condition produces a situation which is the best possible to avoid fatigue fracture of the neck because bending is minimized. Thus, the smallest portion of the neck may be made relatively small in diameter compared to prior art designs and thereby significantly increasing the range of motion between the femoral component and the acetabular bearing before impingement between the neck 7 and the acetabular prosthesis or natural acetabulum. The benefits of such increased motion range were described earlier. The neck is generally conical in shape so that as one moves away from the center of the head 5 bending stresses do not increase.

Figure 2A:
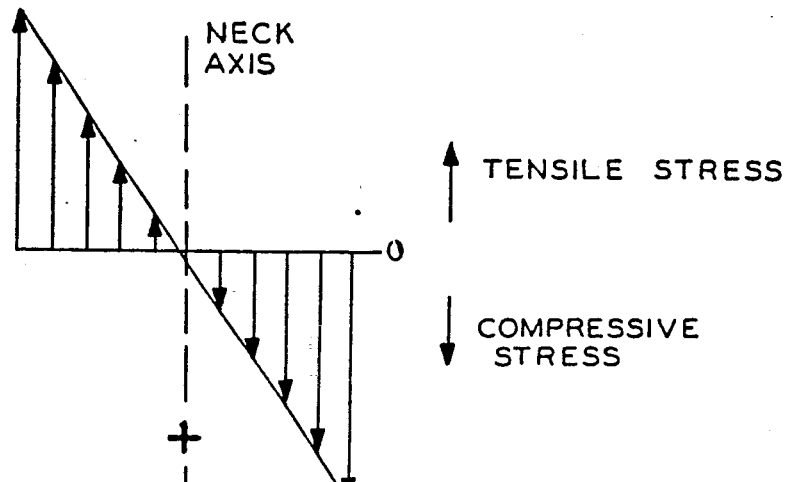
FIGS. 2A, B and C are graphical illustrations of stress conditions resulting from a combination of bending and compression.
Figure 2B:
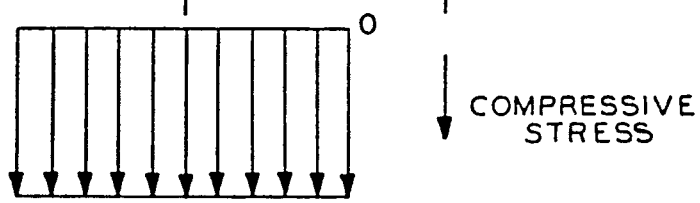
Figure 2C:
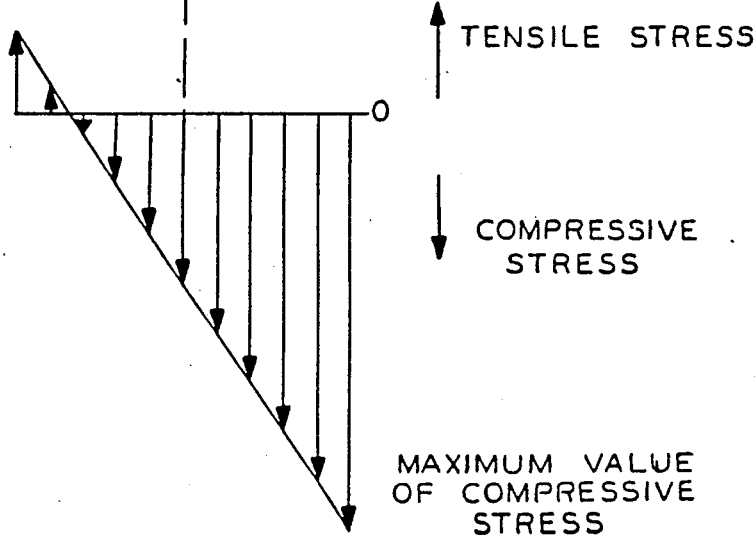
Figure 12:
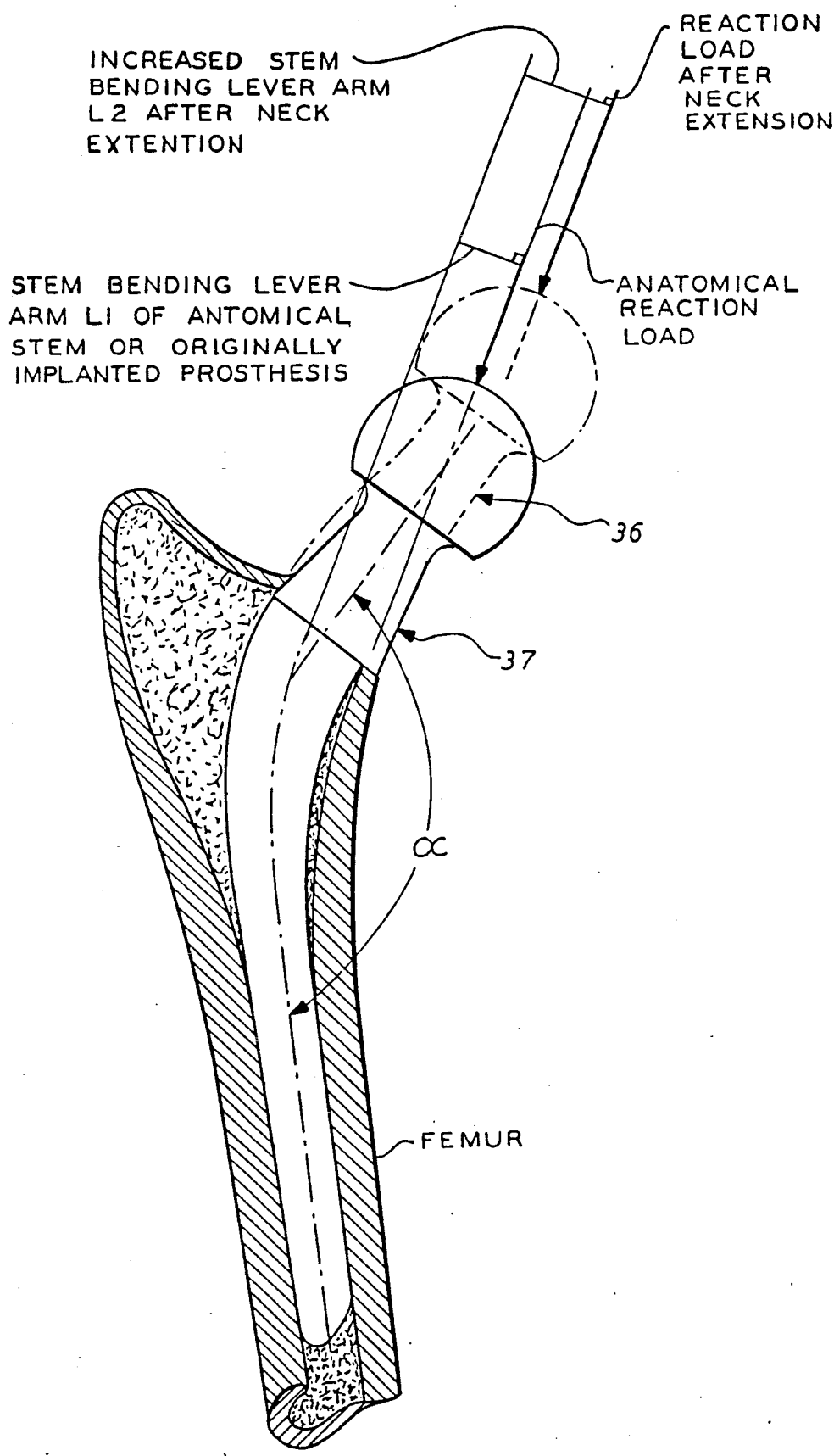
FIG. 12 is a generally cross-sectional view taken in the femoral plane illustrating the effect of extended neck lengthening keeping the neck angle constant.

It may be understood from FIGS. 2A, 2B and 2C that minimizing the bending stress where bending occurs in conjunction with compression not only reduces, or eliminates the tensile component of stress on the lateral surface of the neck but also reduces the compressive stress on the medial surface of the neck. If bending of the neck can be sufficiently reduced, the tensile component introduced on the lateral side will be less than the compressive component on the lateral side and therefore when the two stresses are summed the resultant stress on the lateral side will be compressive thereby eliminating tensile stresses on the lateral surface of the neck. Thus, minimizing bending not only reduces or eliminates tensile stress but also minimizes the maximum value of the compressive stress occurring on the medial surface of the stem.

The neck 7 terminates at the collar 9 which is also shown in FIG. 5 which is a section view taken at section 5—5 of FIG. 4 viewed toward the head. The medial exterior shape 10 of collar 9 closely matches the cross-section of the resected neck of the femur 2 so that the inferior surface 11 of the collar contacts the cortical bone 12 of the resected femur; the resected and prepared femur 2 is shown in FIG. 4.

Figure 3:
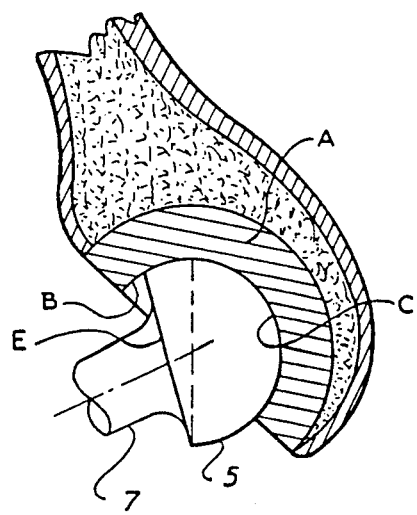
FIG. 3 shows a truncated spherical prosthesis head and illustrates how a truncation edge produces a stress riser in an acetabular bearing.

Given the particular ratio between the neck dimension t and diameter D of the femoral head 5 for articulation with a given acetabular bearing member (e.g. acetabular bearing member A of FIG. 3), as shown in FIG. 6, one can determine the range of motion of the femoral component relative to the acetabular bearing about an arbitrary fixed axis. In general, the smaller the neck dimension t to head diameter D ratio, the larger will be the range of motion for a particular acetabular bearing. This range of motion will in general be dependent on the cross-sectional shape of the acetabular bearing member A (FIG. 3) where this cross-sectional shape is taken perpendicular through an arbitrary axis and passes through the center of the femoral head and will be dependent on the dimension t of the neck at that same particular cross-section when the femoral head and acetabular bearing are in articulation. Since frequently the neck is non-circular in cross-section the dimension t of the neck, and therefore the range of motion, will be dependent on the position of the arbitrary axis relative to the femoral component. The dimension t of the neck is defined herein as the maximum dimension across a minimum area cross-section of the neck.

Another advantage associated with the use of a neck orientation which produces a small neck thickness is that such a small thickness allows the use of a femoral head which is a greater portion of a sphere than can be provided by femoral stems using larger neck dimensions. Let one define a "spherical completeness index" c/r, note FIG. 9, where c is the distance between the truncation plane P and the spherical center 16 and r is the spherical radius, and where the truncation plane is defined as a plane including at least three points on the truncation edge E of the truncated spherical head 5. For conventionally designed stems, this spherical completeness index is approximately 0.5. In the preferred embodiment of the present invention shown this completeness ratio is approximately 0.86 although it will be understood that in accordance with the further teachings of the present invention a ratio greater than 0.5 is an improvement up to approximately 0.95 whereafter it becomes impractical. It is known to those skilled in the art that the greater the spherical completeness ratio, the greater is the dislocation resistance of the head from a socket (e.g. acetabular cup) into which it is assembled. Where, as illustrated in FIG. 10, stem-type prosthesis 1 of the present invention is used in conjunction with an acetabular component 25 (acetabular cup or components of the type shown in the above-noted Averill patent) wherein the femoral head 5 is trapped within the plastic bearing insert 26 received in the acetabular component 25, if the spherical completeness index is relatively large it will provide greater dislocation or separation resistance between the stem and the plastic bearing liner of the acetabular component than a head where this spherical completeness index is relatively small. Thus, the use of a head with a relatively large spherical completeness index c/r provides a stronger connection when it is used in conjunction with the noted acetabular component and bearing insert.

Where one wishes to specify a particular dislocation strength as being adequate, one can use the larger completeness index to improve the range of motion of the acetabular component relative to the stem. It has been found that the strength of such a connection is a function of the head diameter, the overlap angle associated with the acetabular component bearing insert, and the spherical completeness index wherein the strength of the connection increases as these quantities increase. The overlap angle $\theta$ is defined here as the amount of angular engagement between the acetabular bearing A and the femoral head 5 in excess of that produced by the engagement of a femoral head with a hemispherical cavity. Thus, for a given strength requirement one can for a given head size increase the range of motion of the acetabular component by reducing the overlap angle and compensating for this reduction by an increased spherical completeness index. Looking at this another way, if one desires a given dislocation strength for a given head size, if one increases the completeness index one can therefore reduce the overlap angle and thereby increase the range of motion of the acetabular component relative to the stem. This increase in range of motion is desirable since it reduces the possibility of neck cup impingement which can prevent or reduce the internal articulation between the acetabular component and the acetabulum. External articulation is undesirable since it increases acetabular wear. Internal articulation to the maximum extent possible is highly desirable since the whole purpose of the use of a universal type prosthesis is to exchange external for internal motion as disclosed in the Biomedical Engineering Corp. TECHNICAL REPORT noted above.

Further, and referring again to FIG. 3, the larger the spherical completeness index c/r of the present invention reduces the likelihood and frequency of the intrusion of the truncation edge E of the spherical head 5 into the acetabular bearing E thereby minimizing wear resulting from stress concentration effects of such intrusion.

As noted above, FIG. 6, the stem-type femoral prosthesis 1 of the present invention is characterized by a relatively small neck dimension t compared to the head diameter D. The required neck dimension t is related to the head diameter D in that as the head diameter D increases if the neck angle $\alpha$ as shown in FIG. 6 is such that bending occurs, such bending will tend to increase since the distance from the center of the head to the point where the neck is narrowest increases with head size increasing the bending moment of the weakest action arm as shown in FIGS. 7 and 8; the neck angle $\alpha$ being measured between the axis A of the neck 7 and the axis V of the stem 14. Thus, one must have a somewhat larger diameter neck to resist bending where the head is larger. One thus sees in the prior art somewhat smaller neck diameters utilized with 22 mm heads than with 32 mm heads. We have found that by proper selection of the neck angle $\alpha$ and femoral head placement one can reduce bending stresses to the point where under high loading conditions where fatigue is likely to occur tensile stresses are low enough so that one would design to resist compressive stresses wherein higher allowable stresses can be used thereby allowing a smaller diameter neck. Typically this t/D ratio in prior art prostheses is about 0.5. In the invention here, we use a neck thickness to head diameter ratio of about 0.32 for prostheses intended for very heavy individuals to about a ratio of 0.26 for prostheses intended for lighter weight individuals; however, it will be further understood in accordance with the teachings of the present invention that the smaller the ratio the greater the range of motion. It may be seen, therefore, that by proper detailed design of the prosthesis one may achieve much more slender neck thicknesses than is known to the prior art. The preferred ratio is a function of patient weight and the strength of the material used for the neck the ratio increasing with patient weight and decreasing with increasing material strength. The values given are appropriate for ordinary cast cobalt chromium alloy made to ASTM-F75 specification. The use of stronger materials allows still smaller values of this ratio.

A characteristic of an embodiment of the present invention shown in FIG. 6 is that the generator 20 of the surface of revolution which defines the neck shape is a line which is an extension of a line from the center of the head 5 to a point P on the surface of the neck at which the thickness t can be measured. Now if one achieves a situation where there is no tensile stress at the thinnest portion of the neck then there will be no tensile stress anywhere in the neck. This is true if the generator producing the neck shape is always on or outside of a line connecting the center of the head to the point P on the neck. This can be restated in another way. If we define a cone generated by rotating a line from the center of the head to a point on the neck outside surface where the thickness of the neck is measured, then in our design all points on the neck surface are on this cone. This is not true of prior art devices where in all prior art cases points on the neck distally of the region of minimum thickness are inside this cone. With the present invention, therefore, if any part of the neck (e.g. any point on neck cross-section of minimum area) is free of tensile stresses, all parts of or points on the neck will be free of tensile stresses.

Figure 16:
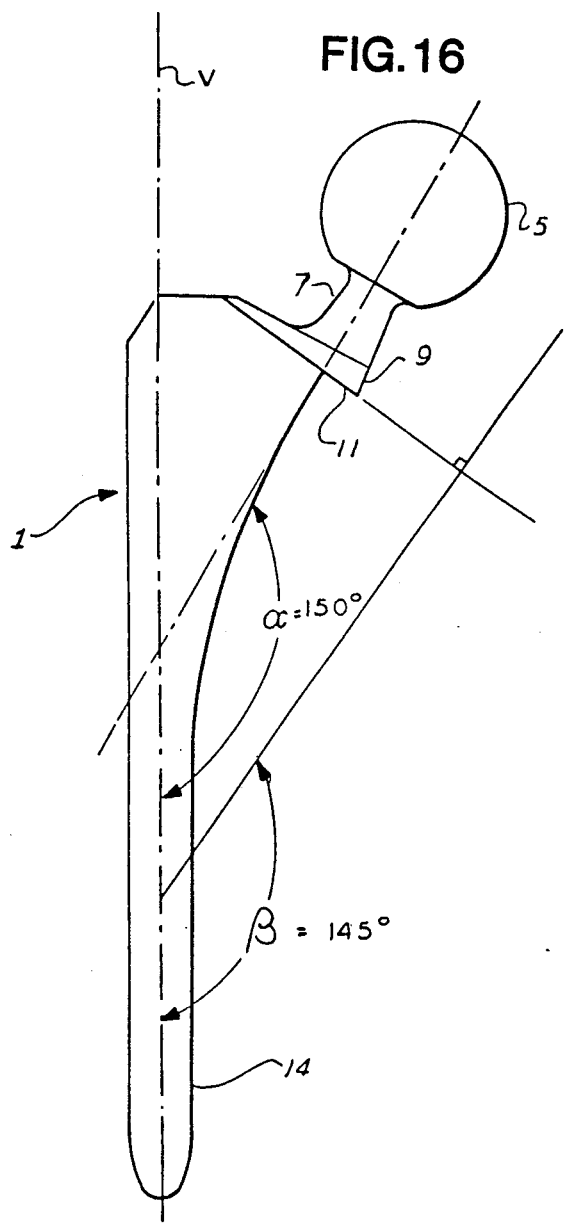
FIG. 16 is an alternate embodiment of a stem-type femoral prosthesis embodying the present invention and including a collar having a more horizontal collar angle $\beta$.

Typically the neck and collar angles of a typical stem-type femoral prosthesis is about 135°. The angle of 135° for both neck and collar is widely accepted in orthopaedics. A collar angle of 135° typically requires the resection of the natural femoral neck perpendicular to the axis of the anatomical neck and this convenient resection orientation is by far the most common neck resection orientation. An embodiment of the present invention using this commonly accepted collar angle is shown in FIG. 6. In the embodiment of the present invention shown in FIG. 6, the neck angle $\alpha$ is preferably about 143° for a neck of standard length with a slightly decreasing neck angle as the neck is extended of the type shown in FIG. 13. An alternate embodiment of the present invention where a somewhat more horizontal collar angle 62 of 145° is used is shown in FIG. 16. The use of this embodiment requires a femoral neck resection which is normally slightly skewed with respect to a perpendicular to the axis of the neck and thus may be slightly less well accepted by some orthopaedic surgeons since it is slightly more inconvenient but the use of the somewhat larger collar angle $\beta$ of 145° allows further bending and shear of the neck. Such obtuse neck angles are described in prior art, for example in the above-noted Treace U.S. patent neck angles as great as 149½° are known. Heimke et al. in U.S. Pat. No. 4,031,571 also disclose a neck angle $\alpha$ which approximates or exceeds that shown in the instant invention; however, the center of the prosthetic head in Heimke is not located at the center of the natural head. A unique characteristic of our neck angle $\alpha$ is that it is greater than in the collar angle $\beta$, the collar angle $\beta$ being measured between the inferior surface 11 of the collar 9 and the stem axis V. This provides for greater medialization of the neck base for a given collar angle $\beta$ than would be likely if, as in the prior art such as described in the above-noted Charnley and Treace patents and in U.S. Pat. No. 4,068,324 issued Jan. 17, 1978 to Charles A. Townley et al., the neck angle $\alpha$ was equal to or less than the collar angle $\beta$. Thus, for a given collar angle $\beta$ the use of a neck angle $\alpha$ which is greater than the collar angle $\beta$ reduces bending stresses on the neck (compared to a design in which the neck angle $\alpha$ is less than or equal to the collar angle $\beta$) and allows the use of a smaller diameter neck with its attendant benefits of increased range of movement, etc. noted above. In the preferred embodiment shown in FIG. 14, extended neck prostheses are made by moving the head away from the stem along line B inclined at an angle $\gamma$ of about 24° from the femoral stem axis, thus minimizing the effect of neck length on stem loading during high loading activity phases since during such phases the reaction projection of load vector in the femoral plane is approximately coincident with this line.

Another characteristic of the instant invention is that the base of the neck 7 is somewhat smaller than the superior surface of the collar 9 to which it is attached and the base of the neck is oriented in an extreme medial position relative to the collar, note FIG. 1. Nowhere in the prior art is this condition known to exist. The only instances in the prior art where the generator (FIG. 6) of the neck shape is coincident with the edge of the collar is where the base of the neck is in effect the collar. The use of a neck base which is smaller than the collar and the extreme medialization of the neck relative to this larger collar allows the use of a relatively large collar which allows effective transfer to bone, along with a relatively large neck angle and small diameter neck with their attendant benefits.

The extreme medialization of the neck of the subject invention produces a small medial stem distance $d_1$ (FIG. 6) which is measured from the axis A of the neck 7 to the most medial point on the stem 14 in the femoral plane and a medial collar distance $d_2$ which is measured from the neck axis to the most medial point on the collar 9 in the femoral plane. Making this distance non-dimensional by dividing these distances by the head 5 diameter D in order to consider the effect of femoral component size, prior art prostheses typically utilize a medial stem distance $d_1$ to head diameter D ratio value of 0.3. In the subject invention for the preferred embodiment shown in FIG. 6 using the widely employed collar angle $\beta$ of 135°, this value is approximately 0.12 and in the alternate embodiment shown in FIG. 16 using the larger collar angle $\beta$ of 145° the medial stem distance $d_1$ is essentially zero (0). The medial collar distance $d_2$ to head diameter D ratio of prior art inventions is typically 0.4 while in the subject invention in the preferred embodiment shown the medial collar distance ratio has a value of about 0.25 and in the alternate embodiment of FIG. 16 a value of 0.22. Thus, it will be seen that a reduction in collar angle $\beta$ produces a neck configuration less subject to bending.

Further, it may be seen that an extension of the medial neck curve, defined as the medial aspect of the neck surface defined by the edge of the cross-section taken in the femoral plane excluding the fillet radii connecting the medial neck curve to the collar and head where such curve is extended by a tangent curve of similar shape passes through the most medial point on the inferior surface of the collar in the femoral plane as distinct from the neck and not simply the inferior surface of the neck as for example in the prostheses shown in the Heimke et al. and Townley patents noted above. The medial neck curve passes laterally of the medial collar point and thus further medialization and reduction of the collar distance $d_2$ is possible. The preferred embodiment shown in the subject invention may be further improved only by allowing this medial neck shape and neck axis to be rotated counterclockwise about the center of the head as shown in FIG. 1 until the curve passes through the most medial point on the superior surface of the collar. Further medialization of the neck by such continued rotation is possible but such further rotation given a particular neck cone angle will result in truncation of the cone with resultant weakening of the neck or the intrusion of the neck into the space beyond the borders of the bone formerly occupying its normal anatomical location as shown in FIG. 8. Although such additional rotation may be permissible or even desirable, the embodiment shown nevertheless does produce a substantial improvement in range of motion and neck reduction compared to prior art prostheses. It may be seen from FIG. 8 that the noted rotation produces a negative medial stem distance. Further rotation can also produce a negative medial collar distance.

Figure 14:
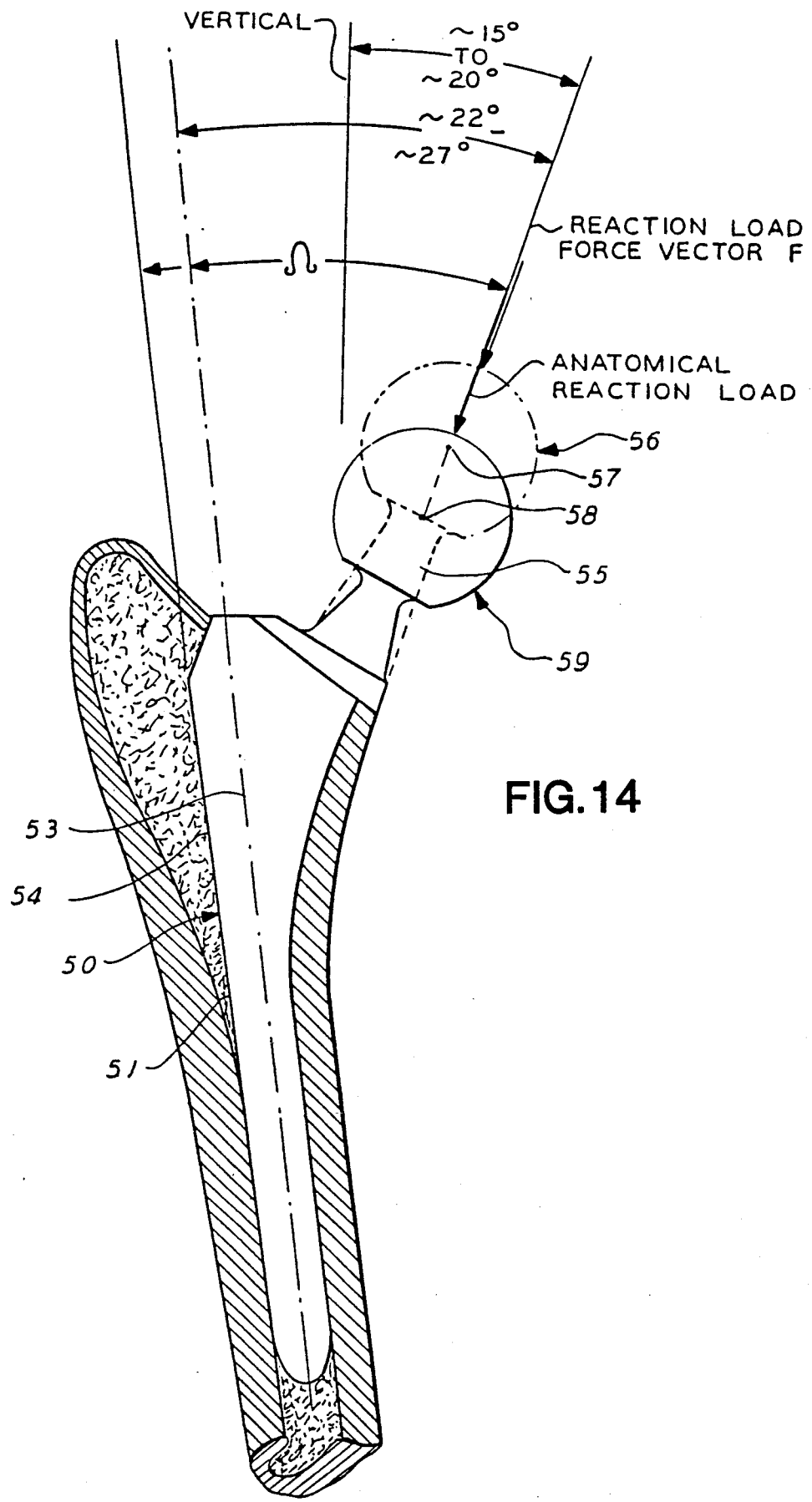
FIG. 14 is a generally cross-sectional view taken in the femoral plane illustrating the effect of neck lengthening by extending the neck along the action load line.

The present invention also provides a solution to the above-noted leg or limb shortening-revision prosthesis problem. In accordance with the teachings of the present invention, it has been discovered that if the neck of a revision prosthesis is extended along the line of action of the reaction load force vector F as shown in FIG. 14, this problem is overcome. It is well known to those skilled in the art that for the purposes of load analysis force vectors can be treated as sliding vectors and that the point of application of the load is unimportant in load calculations and that the application of a load anywhere along a given line of action is equivalent to application of the load at any other point along such line. Thus, the placing of the center of the head of an extended neck prosthesis anywhere along the line of action will not affect the bending moment on the stem (such as the stem 51 of the stem-type femoral prosthesis 50 shown in FIG. 14), the muscle forces, or joint reaction forces. Since in the present neck extension invention the angle $\Omega$ of the reaction load vector F (acting through the head center 57 of the extended neck or revision prosthesis 56 shown in dashed outline and the head center 58 of the originally implanted prosthesis 59) with respect to the stem axis 53 or the lateral edge 54 does not vary, a change in neck length (such as the increased or extended neck 55 of the revision prosthesis 56 shown in dashed outline) using this teaching will produce no change in loading for one particular phase of human activity (e.g. walking or standing or etc.). Since it is most important to reduce relatively high stem bending loads and maintain muscle effectiveness during high loading activity phases, the neck extension in accordance with the teaching of the present invention is along a line coinciding with the reaction load direction associated with high joint reaction loads, namely along a line inclined in the femoral plane about 15° to 20° from vertical or approximately inclined in the femoral plane from 22° to 27° from the stem axis such as axis 53 in FIG. 14 and preferably inclined at approximately 24° with respect to the stem axis. It will be understood that this invention or teaching is equally applicable to a stem-type femoral prosthesis having a curved stem as disclosed in U.S. Pat. No. 4,279,042 issued July 21, 1981 to Andriacchi et al. and as shown in FIG. 15.

Figure 13:
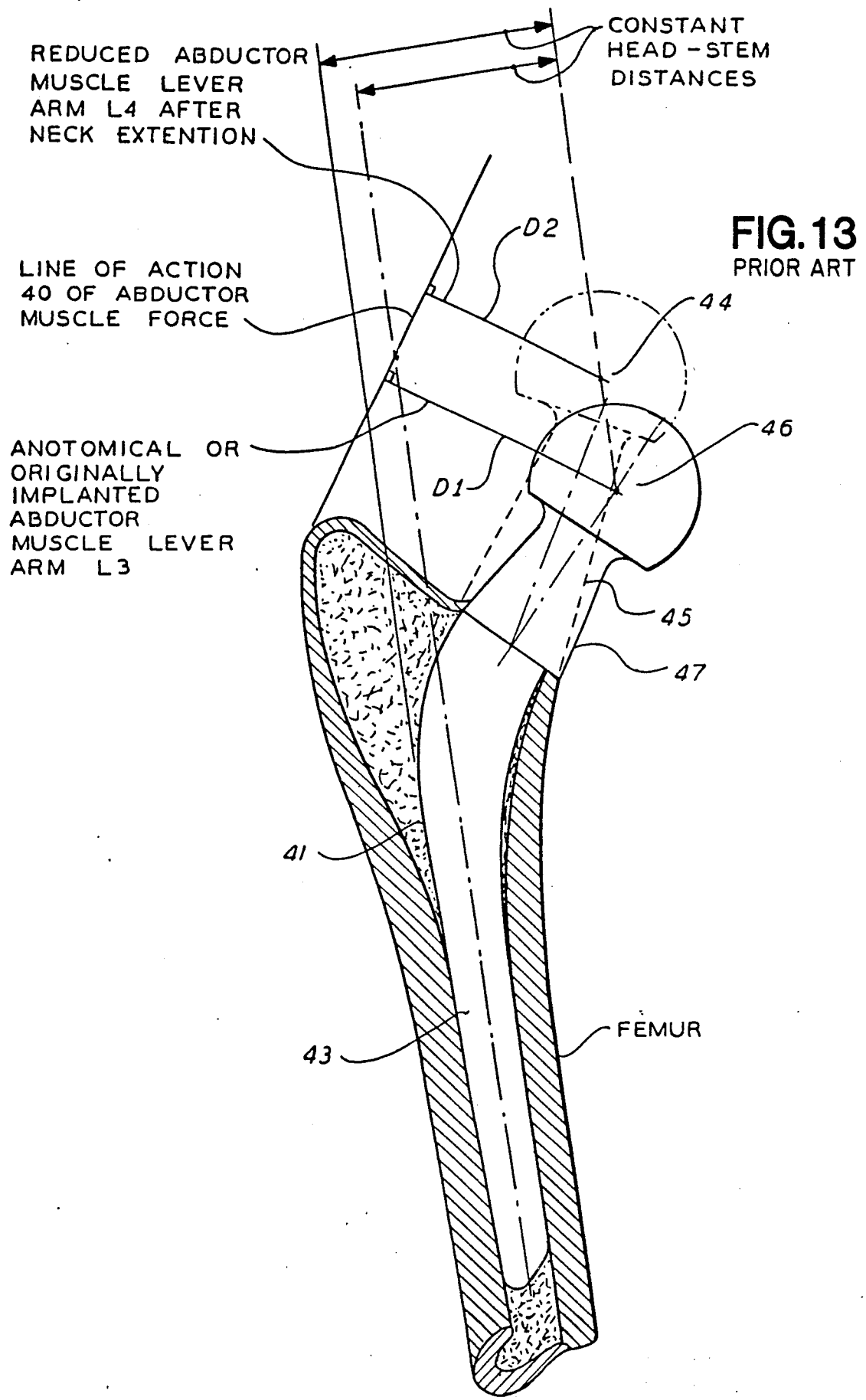
FIG. 13 is a generally cross-sectional view taken in the femoral plane illustrating the effect of neck lengthening keeping the head-stem distance constant.
Figure 15:
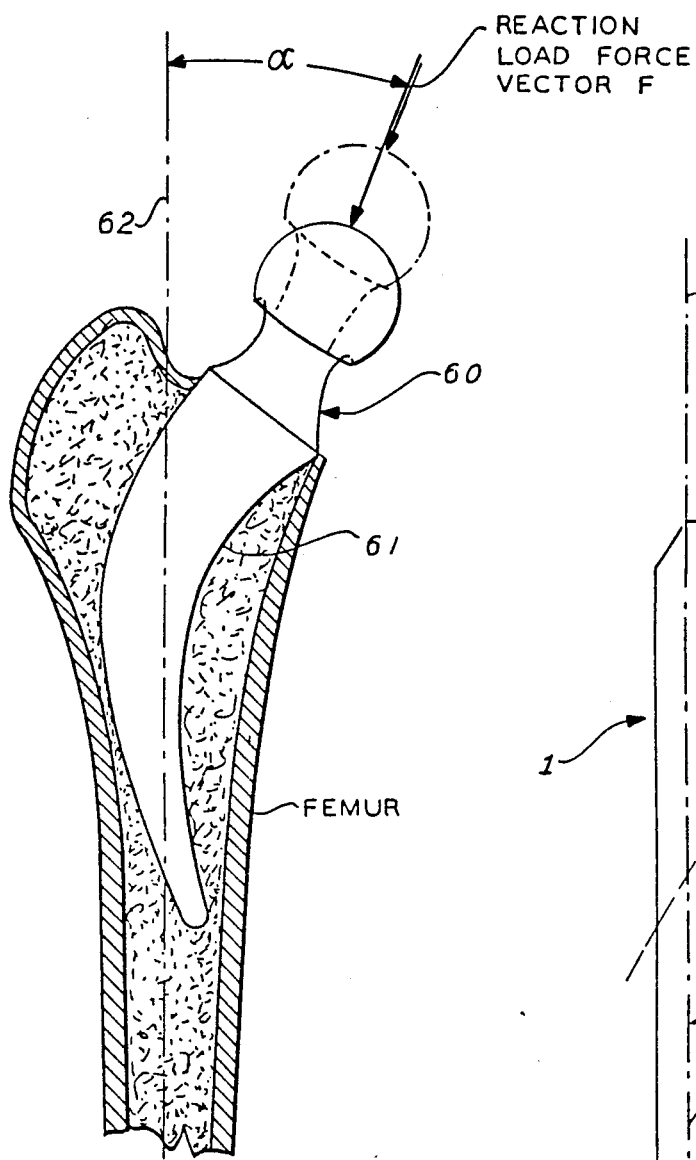
FIG. 15 is a generally cross-sectional view taken in the femoral plane of a stem-type femoral prosthesis having a curved stem and illustrating the definition of the angle $\Omega$ of the reaction load vector F for a curved stem which angle $\Omega$, as shown, is measured between the reaction load force vector F and the longitudinal axis 62 of the femur upon the curved stem prosthesis being implanted in its normal position in the femur.

Referring to FIG. 15, it will be understood that although the curved stem 61 of the stem-type femoral prosthesis 60 does not have a longitudinal axis in the sense that the straight stems shown in FIGS. 13 and 14 respectively have longitudinal axes 43 and 53, the angle $\Omega$ is measured between the reaction load vector F and the longitudinal axis 62 of the femur after the prosthesis 60 is implanted in its normal position in the femur.

In the context of the specification and appended claims, the term extended neck prostheses, or prostheses, is used to include all such immediately above-described prostheses.

It will be further understood by those skilled in the art that many modifications and variations of the present invention may be made without departing from the spirit and the scope thereof.

What is claimed is:

1. A femoral prosthesis for replacing a natural femoral neck and a natural femoral head of a femur, said femur having a medullary cavity, said prosthesis comprising:
    an elongated stem for placement in the medullary cavity of the femur, said stem having a longitudinal axis;
    a collar disposed at a proximal portion of the stem, said collar extending outwardly from said stem to define an inferior bearing surface and to define a medial edge;
    a neck extending from said stem and said collar and inclined between 25°-35° medially from the stem; and
    a head extending from a portion of the neck remote from said collar, said head defining a truncated sphere terminating at a truncation edge, wherein at least three points on said truncation edge define a truncation plane adjacent said neck, said head having a spherical radius r, a spherical center and a distance c measured perpendicularly between the truncation plane and the spherical center, the ratio c/r being greater than 0.7, and wherein substantially all of the neck is disposed laterally of a radially aligned line passing from the spherical center of the head to the medial edge of the collar, whereby the ratio c/r and the alignment of the neck relative to the stem and to the radius extending to the medial edge of the collar enhances the range of articulation of said femur and the resistance of the prosthesis to bending stress and dislocation.

2. A prosthesis as in claim 1 wherein a line extending perpendicular to the inferior face of the collar and intersecting the stem axis is medially off-set from the stem axis at an angle which is not less than the angle between the stem axis and the neck axis.

3. A prosthesis as in claim 1 wherein the stem includes a medial surface which intersects the inferior surface of the collar, the axis of the neck being substantially aligned with the intersection of the medial surface of the stem with the inferior surface of the collar.

4. A prosthesis as in claim 1 wherein the spherical head defines a diameter D, and wherein the neck defines a minor cross-sectional dimension t substantially adjacent the intersection of the head and the neck, the ratio t/D being between approximately 0.26 and 0.32.

5. A prosthesis as in claim 1 wherein the neck includes a medial surface generally adjacent to the radius extending from the spherical center to the medial edge of the collar.

6. A prosthesis as in claim 1 wherein the ratio c/r is approximately 0.86.

7. A femoral prosthesis for replacing a natural femoral neck and a natural femoral head of a femur, said femur having a medullary cavity, said prosthesis comprising:
    an elongated stem for placement in the medullary cavity of the femur, said stem having a longitudinal axis, a collar disposed at a proximal portion of the stem, said collar extending outwardly from said stem to define an inferior bearing surface;
    a neck extending from said stem and said collar and inclined between 25°-35° medially from the stem, said stem defining an outer surface and an area of minimum cross-sectional dimension at a location thereon remote from said collar; and
    a head extending from a portion of the neck remote from said collar, said head defining a truncated sphere terminating at a truncation edge, wherein at least three points on said truncation edge define a truncation plane adjacent said neck, said head having a spherical radius r, a spherical center and a distance c measured perpendicularly between the truncation plane and the spherical center, the ratio c/r being greater than 0.7, said head and said neck being disposed such that no portions of the outer surface of said neck are disposed within a cone generated from the spherical center and passing through the area of minimal cross-sectional dimension on the neck, whereby the ratio c/r, the alignment of the neck to the stem and the disposition of the head and neck relative to one another enhances the range of articulation of the femur and the resistance of the prosthesis to bending stress and dislocation forces.

8. A prosthesis as in claim 7 wherein the ratio c/r is approximately 0.86.

* * * * *